United States Patent [19]

Schüller

[11] Patent Number: 5,441,522
[45] Date of Patent: Aug. 15, 1995

[54] PACEMAKER

[75] Inventor: Hans Schüller, Lund, Sweden

[73] Assignee: Hans Schuller, Lund, Sweden

[21] Appl. No.: 120,561

[22] Filed: Sep. 13, 1993

[30] Foreign Application Priority Data

Sep. 14, 1992 [SE] Sweden ................ 9202630

[51] Int. Cl.$^6$ .................................. A61N 1/36
[52] U.S. Cl. ................................... 607/9
[58] Field of Search ........................ 607/9, 25

[56] References Cited

U.S. PATENT DOCUMENTS

| | | | |
|---|---|---|---|
| 4,312,355 | 1/1982 | Funke . | |
| 4,421,116 | 12/1983 | Markowitz | 607/9 |
| 5,086,774 | 2/1992 | Duncan | 607/9 |
| 5,282,838 | 2/1994 | Hauser et al. | 607/9 |
| 5,318,594 | 6/1994 | Limousin et al. | 607/9 |

FOREIGN PATENT DOCUMENTS 9204076  3/1992  WIPO ................ 607/9

OTHER PUBLICATIONS

"Hemodynamic Consequences of Atrioventricular and Ventriculoaxial Pacing", Ogawa et al., PACE, vol. 1, pp. 3–15, 1973.

Primary Examiner—William E. Kamm
Assistant Examiner—Jeffrey R. Jastrzab

[57] ABSTRACT

A pacemaker for stimulating both the atrium and the chamber of a heart is able to inhibit the emission of chamber stimulating pulses if a spontaneous chamber reaction is sensed before the expiry of an AV interval, counting from the emission of an atrial stimulating pulse. To prevent the pacemaker from being locked in a position where consecutive chamber stimulating pulses are emitted because of retrograde atrial reactions making the atrium insensitive to atrial stimulating pulses, the AV interval is shortened after the emission of a chamber stimulating pulse. After a predetermined time, a predetermined number of pulses, or when a spontaneous chamber reaction is sensed within the shortened AV interval, the longer AV interval is restored.

7 Claims, 3 Drawing Sheets

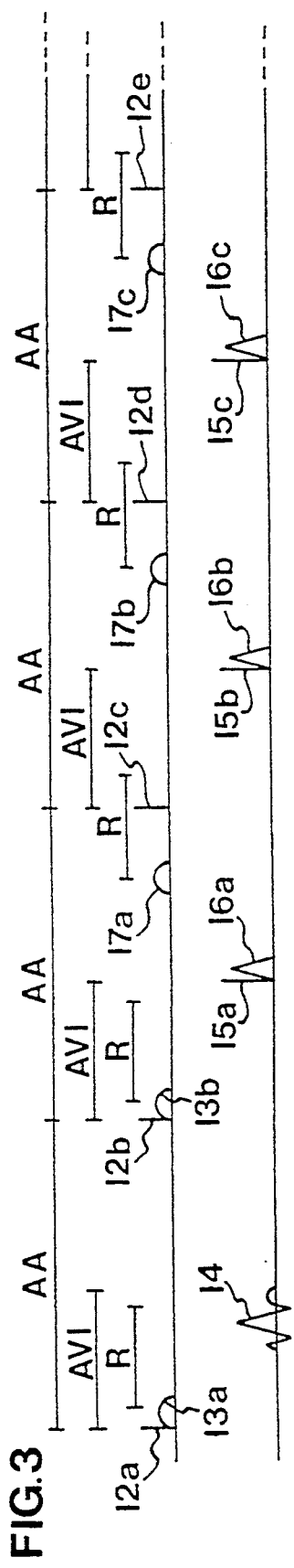
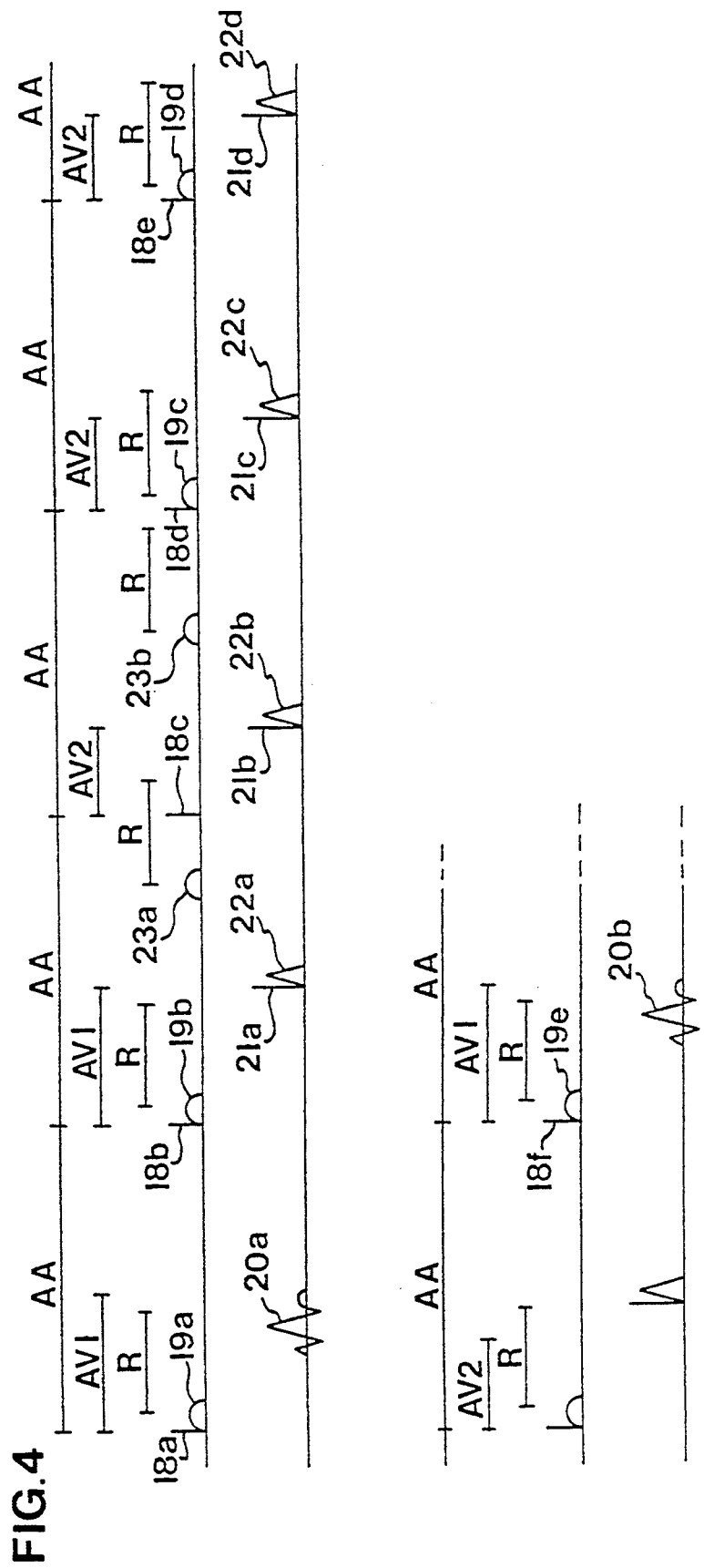
FIG.3
FIG.4

PACEMAKER

BACKGROUND OF THE INVENTION

The present invention relates to a pacemaker comprising a first electrode lead disposed in one atrium of a heart for stimulating atrial reactions. A second electrode lead is disposed in one chamber of the heart for stimulating and sensing chamber reactions. A stimulating pulse generator is provided for generating and emitting stimulating pulses to the atrium and the chamber via said first and said second electrode lead, respectively. A control device controls the emission of stimulating pulses and the sensing reactions. After each emitted atrial stimulating pulse, the control device starts an AV interval having a first duration, after the expiry of which a chamber stimulating pulse is emitted if no chamber reaction has been sensed during said AV interval.

A pacemaker of this type is disclosed in U.S. Pat. No. 4,312,355 and comprises a stimulating pulse generator which generates stimulating pulses, a first electrode which is disposed in one atrium of a heart, a second electrode which is disposed in one chamber of the heart, and a control device for controlling the different functions of the apparatus. Via the first electrode, stimulating pulses can be supplied to the atrium for stimulating an atrial reaction, and spontaneous atrial reactions can be sensed. In the same way, chamber reactions can be stimulated and sensed via the second electrode. The pacemaker according to the U.S. '355 patent has an inhibitory function, i.e. if a chamber reaction has been sensed within the AV interval after an atrial reaction (spontaneous or stimulated), no chamber stimulating pulse will be emitted. The same applies to atrial stimulations in relation to chamber reactions, i.e. if an atrial reaction has been sensed within the AV interval, no atrial stimulating pulse will be emitted.

Basically, a healthy heart functions as follows. The atrium contains the SA node or the sinus node. The sinus node is able itself to be depolarized at a regular rhythm, which may vary depending on factors such as physical activity and state of health. Depolarization of the sinus node results in a depolarization of the atria which then contract and pump blood into the chambers. Depolarization pulses continue via a plurality of conduction systems to the AV node, or the atrioventricular node, which is located in the area between atrium and chamber. The depolarization pulse is conducted via the AV node to the conduction systems in the chambers, which contract and pump the blood out into the systemic circulation and the pulmonary circulation, respectively. The atrium and the chamber are thereafter repolarized, and are then susceptible to the next depolarization pulse from the SA node.

In patients having a non-functioning, or a poorly functioning sinus node, a so-called sick sinus node syndrome, the atrium thus has to be stimulated regularly by the pacemaker. Even if the AV node has a normal function, a double-chamber pacemaker is sometimes implanted as a safety precaution, where the chamber electrode is used for stimulation only when temporary disorders or problems arise in the AV node, such as a delay of the AV conduction on account of vasovagal reactions.

Physiologically, the conduction time in the AV node is within the range 120–220 ms. In order not to stimulate the chamber unnecessarily, it is therefore necessary to program pacemakers with an inhibitory function for chamber stimulation using a long AV interval. AV intervals of up to 250 ms are not unusual.

A long AV interval entails that when a chamber stimulating pulse is actually emitted, the atria may already have been repolarized. There is then the risk that a retrograde conduction with ensuing depolarization of the atria follows the chamber stimulation. When the next atrial stimulating pulse is emitted, the atrium may be in its biological repolarization phase and then is unsusceptible to a normal stimulating pulse. Hence, there will be no depolarization or any conduction to the chamber. After the AV interval has expired, the chamber is therefore stimulated anew. The pacemaker may then be locked in a loop where the chamber is continuously stimulated after each AV interval, despite the fact that the patient would normally not need such stimulation. Apart from discomfort to the patient, there is an increase in the consumption of power from the battery in the pacemaker which then is discharged more rapidly than if the intended function of the pacemaker, i.e. to stimulate only the atrium, could be maintained.

In patients having a pacemaker with a frequency varying depending on the level of activity of the patient, the retrograde conduction time need not be very long before these problems occur.

SUMMARY OF THE INVENTION

An object of the invention is to provide a pacemaker which automatically prevents a temporary delay in the normal AV conduction from giving rise to a situation where the chamber is continuously stimulated after the termination of each AV interval.

According to the invention, this object is achieved by providing a pacemaker having a first electrode lead disposed in an atrium of a heart for stimulating atrial reactions. A second electrode lead is disposed in a chamber of the heart for stimulating and sensing chamber reactions. A stimulating pulse generator generates and emits stimulating pulses to the atrium and chamber via the first and second electrode leads. A control device controls the emission of the stimulating pulses and senses the chamber reactions. After each emitted atrial stimulating pulse, the control device starts an AV interval having a first duration. A chamber stimulating pulse is emitted after expiration of the AV interval if no chamber reaction has been sensed during the AV interval. When a chamber stimulating pulse is emitted, the first duration of the AV interval is replaced with a second duration which is shorter than the first duration.

When a delay in the normal AV conduction occurs and the chamber is stimulated after the expiry of the AV interval, e.g. 250 ms, the AV interval is shortened for the next pulse to, for example, 150 ms. A retrograde conduction, caused by the chamber stimulation, with ensuing depolarization of the atrium may, if the atrium has not already been repolarized, result in the absence of atrial depolarization for the following atrial stimulating pulse. As a result of the shortened AV interval, the next chamber stimulation occurs after 150 ms and not 250 ms. Even if a retrograde conduction now also occurs, the atrium will be much more susceptible to complete repolarization before the next atrial stimulating pulse is emitted.

To return to the normal inhibitory function with a longer AV interval, the pacemaker according to an advantageous further development of the invention is so designed that the control device, after switching to the second duration of the AV interval, replaces the second duration with the first duration if a chamber reaction is sensed during said second duration of said AV interval after the emission of an atrial stimulating pulse.

Alternatively, such a return procedure can be effected by the control device, after a predetermined number of pulses, replacing the second duration of the AV interval with the first duration.

A further possibility is achieved by the control device, after a predetermined time, resetting the AV interval to the first duration.

The first duration of the AV interval is preferably between 240 and 260 ms, and the second duration of the AV interval is preferably between 140 and 190 ms.

BRIEF DESCRIPTION OF THE DRAWINGS

An embodiment of the pacemaker according to the invention will be described in more detail hereinbelow with reference to the drawings, in which

FIGS. 3 and 4 are diagrams showing stimulating pulses and depolarizations in a heart.

DESCRIPTION OF THE PREFERRED EMBODIMENT

Figure 1:
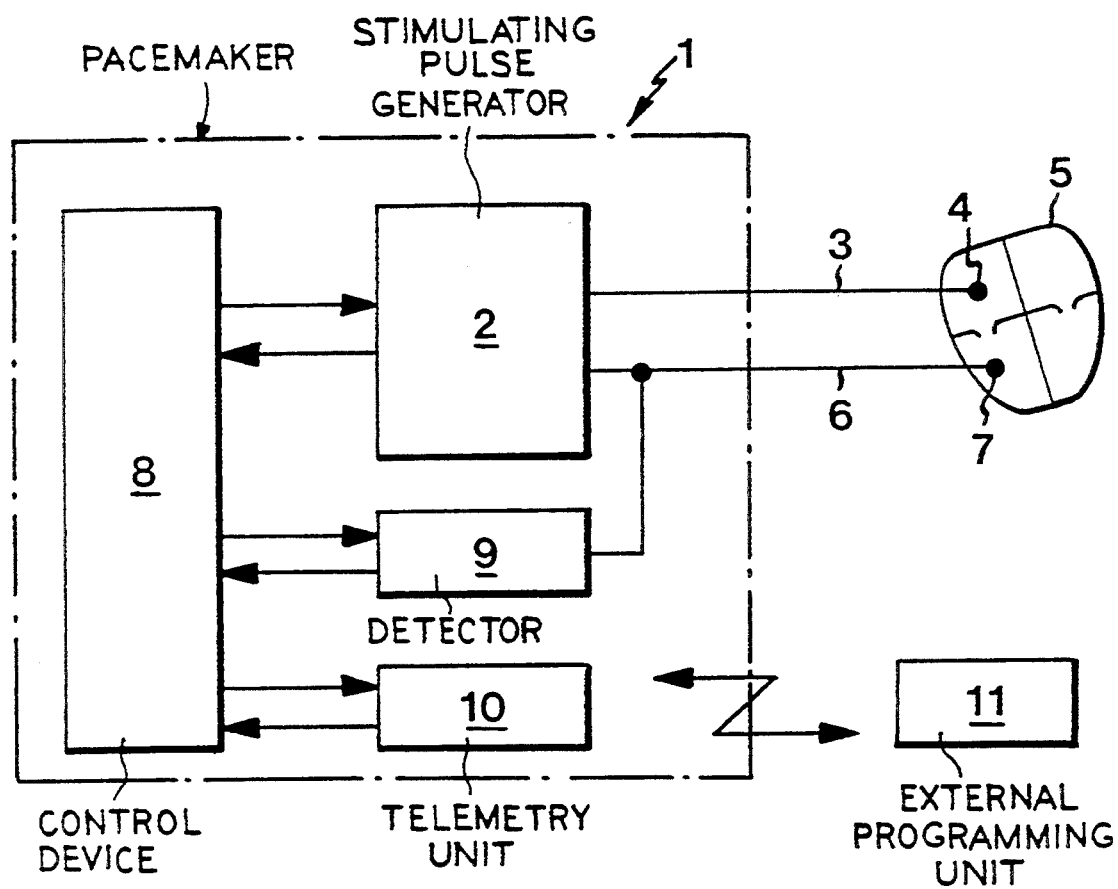
FIG. 1 is a block diagram of the pacemaker.

A pacemaker 1 according to the invention comprises, as shown in FIG. 1, a stimulating pulse generator 2 which generates stimulating pulses and supplies them via a first electrode lead 3 and a first electrode tip 4 to one atrium in a heart 5 or via a second electrode lead 6 and a second electrode tip 7 to one chamber of the heart 5. A control device 8 controls the emission of stimulating pulses by the stimulating pulse generator 2. The control device 8 also controls the energy content and the duration of the stimulating pulses. A detector 9 for sensing chamber reactions is connected to the second electrode lead 6. Information about sensed reactions is transmitted to the control device 8 which then inhibits the emission of chamber stimulating pulses after the expiry of an AV interval which is started after each atrial stimulating pulse emitted. The control device 8 also determines the time when the detector 9 is operative for sensing spontaneous reactions in the chamber. Via a telemetry unit 10, the control device 8 can be programmed or reprogrammed from an external programming unit 11 by a doctor.

In a patient having a non-functioning sinus node, the atrium must be stimulated regularly. If the AV node has a normal function, the second electrode lead 6 and the second electrode tip 7 serve as a stand-by in case the AV node, for some reason or other, should temporarily have an impaired function. As long as the AV node functions, the control device 8 inhibits the emission of chamber stimulating pulses. This is done in such a manner that the detector 9 senses the chamber after an atrial stimulating pulse has been emitted; if a spontaneous chamber reaction is sensed within the AV interval, the emission of the ventricular stimulating pulse is inhibited. If, on the other hand, no spontaneous reaction is sensed within the AV interval, the control device 8 commands the emission of a stimulating pulse to the chamber.

The natural AV conduction normally is in the interval 120–220 ms. In order not unnecessarily to stimulate the chamber, sensing by means of the detector 9 should thus take place by a certain margin to the maximum interval time, e.g. by using an AV interval of 250 ms.

FIG. 3 is a diagram showing what may occur in a heart connected to a conventional pacemaker if the natural AV conduction, for some reason or other, is delayed, or if there is no such conduction at all.

An atrial stimulating pulse 12a is emitted at the beginning of the upper time axis, which represents events in the atrium. The atrial stimulating pulse 12a gives rise to an atrial depolarization, shown in the diagram as a stimulated P wave 13a. The atrium has a biological recovery time R during which it is repolarized, the so-called refractory period. At the same time as the atrial stimulating pulse 12a is emitted, the count-up of an AV interval having the length AV1 starts. In the lower time axis, which represents events in the chamber, it appears that a spontaneous chamber repolarization in the form of a QRS wave 14 occurs before the AV interval has expired, and that no chamber stimulating pulse is therefore emitted.

After the expiry of an AA interval, which indicates the distance in time between two consecutive atrial stimulations and which was started with the atrial stimulating pulse 12a, the following heart pulse cycle commences with an atrial stimulating pulse 12b, which gives rise to a P wave 13b. On account of e.g. a vasovagal reaction in the heart, the natural AV conduction is delayed and the AV interval expires without any spontaneous QRS wave having been sensed. A chamber stimulating pulse 15a is therefore emitted, which gives rise to a stimulated chamber depolarization 16a.

As a result of the chamber depolarization 16a, a retrograde conduction to the atrium can also take place. Since the size of the AV interval was on the large side, the atrium will in this case already have been repolarized, which entails that the retrograde conduction may give rise to a new atrial depolarization, shown as a retrograde P wave 17a. If the next atrial stimulating pulse 12c is emitted before the atrium has again been repolarized, no depolarization is stimulated since the atrium is unsusceptible to stimulation during the refractory period R, and consequently there will be no spontaneous AV conduction. This means that the AV interval expires, a chamber stimulating pulse 15b being emitted which results in a stimulated chamber depolarization 16b. The atrium has now however again been repolarized and there is room for a new retrograde P wave 17b. The next atrial stimulating pulse 12d also becomes ineffective, and after the expiry of the AV interval, a new chamber stimulating pulse 15c is emitted, resulting in a stimulated chamber depolarization 16c. The retrograde P wave 17c with the following ineffective atrial stimulating pulse 17e indicates that the pacemaker has been locked in a loop.

FIG. 4 shows how the pacemaker 1 automatically solves this problem. The starting point is the same as in FIG. 3. An atrial stimulating pulse 18a is followed by a stimulated P wave 19a. A spontaneous QRS wave 20 appears before the AV interval of the duration AV1 has expired.

After the next atrial stimulating pulse 18b and stimulated P wave 19b, no spontaneous QRS wave is sensed before the AV interval has expired and a chamber stimulating pulse 21a is emitted. This pulse results in a stimulated chamber depolarization 22a. After the emission of the chamber stimulating pulse 21a, the control device 8 in the pacemaker 1 replaces the duration AV1 for the AV interval with a shorter duration AV2, being e.g. 150 ms.

As in FIG. 3, a retrograde P wave 23a now occurs, which entails that the next atrial stimulating pulse 18c becomes ineffective, since it is emitted during the refractory period R. After the AV interval of the new duration AV2 has expired, a chamber stimulating pulse 21b is emitted, which in this case occurs 100 ms earlier than in FIG. 3. In this case too, a retrograde P wave 23b occurs, since the atrium has already been repolarized because of the preceding retrograde P wave 23a. The interval from the retrograde P wave 23b to the next atrial stimulating pulse 18d is now longer, thanks to the chamber stimulating pulse 21b coming earlier, and the atrium now has time to be repolarized before the next atrial stimulating pulse 18d is emitted. A stimulated P wave 19c now occurs, and the possibilities of a normal AV conduction have been restored.

Since the AV interval is relatively short, it is however not certain that a spontaneous QRS wave occurs before the AV interval has expired. A chamber stimulating pulse 21c is then emitted and gives rise to a stimulated chamber depolarization 22c.

From FIG. 4, it appears that after four consecutive AV intervals of the length AV2, the pacemaker returns to the AV interval of the length AV1 in order to check whether the temporary disturbance of the AV conduction has ceased. An atrial stimulating pulse 18f with a stimulating P wave is followed by a spontaneous QRS wave 20b before the AV interval has expired and the pacemaker can proceed with a maintained long AV interval.

The number of consecutive AV intervals of shorter duration can be determined by the doctor for the respective patients and is transmitted via the programming unit 11 to the control device 8, as is the length of the AV1 and AV2 durations, respectively. Preferably, use is made of less than 15 consecutive AV intervals of the duration AV2.

Figure 2:
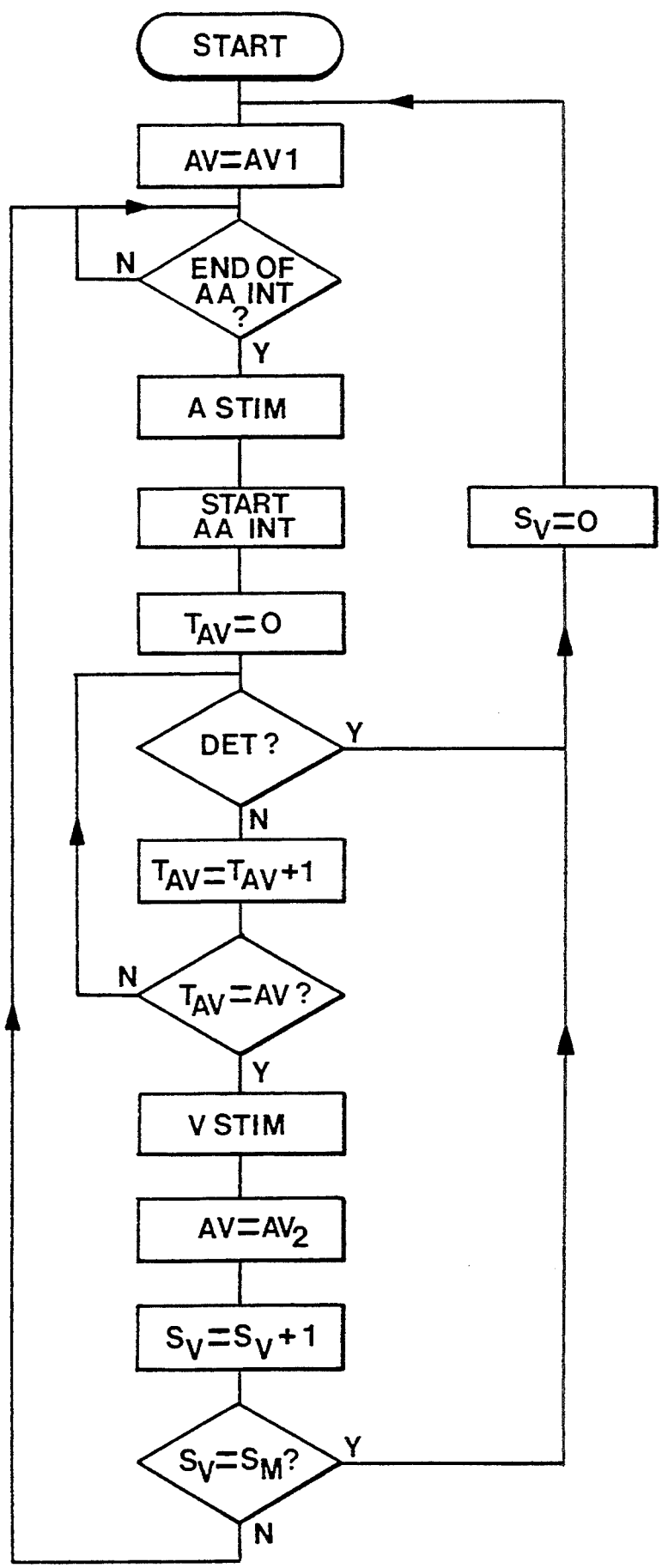
FIG. 2 is a flow diagram comprising the most essential functional stages of the pacemaker.

The flow diagram in FIG. 2 illustrates the function of the pacemaker 1. The START block indicates symbolically that the pacemaker 1 is activated, including several functional stages which are not directly related to the function according to the invention. In one stage, a value for the AV interval (AV=AV1) is however allocated and the AA interval in the block END OF AA INT? is checked. When the AA interval has expired, the atrium is stimulated, which is indicated by A STIM. After an atrial stimulating pulse A STIM has been emitted, the count-up of a new AA interval (START AA INT) is initiated as well as a time counter for the AV interval ($T_{AV}=0$). Both are implemented functions of the control device 8. The control device 8 senses in the block DET? if any chamber reaction has occurred. As long as there is no chamber reaction (output N), the time counter is counted up ($T_{AV}=T_{AV}=1$) and it is checked whether the AV interval has expired ($T_{AV}=AV?$).

If a chamber reaction is sensed before the AV interval has expired (output Y), a counter for the number of emitted chamber stimulating pulses ($S_V=0$) is reset to zero and the AV interval is set at AV1, i.e. the longer interval.

If no chamber reaction has been sensed before the AV interval has expired (output Y in the block $T_{AV}=AV?$), a chamber stimulating pulse (V STIM) is emitted and the Av interval is set at AV2. The counter for the number of emitted chamber stimulating pulses is counted up ($S_V=S_V+1$). If the number of consecutive chamber stimulating pulses amounts to a predetermined number ($S_V=S_M?$), the number of emitted chamber stimulating pulses ($S_V=0$) is reset to zero and the AV interval is set at AV1. If the number of consecutive chamber stimulating pulses falls below the predetermined number (output N), the AV interval is not changed.

Whether a chamber stimulating pulse has been emitted or a spontaneous chamber reaction has occurred, the expiry of the AA interval is awaited before the next atrial stimulating pulse is emitted and the entire functional block is again initiated. The longer AV interval AV1 will thus, in accordance to the flow diagram, be restored, either after a predetermined number of consecutive chamber stimulating pulses $S_N$, or when a spontaneous chamber reaction occurs within the AV interval having the duration AV2, and the AV2 duration of the AV interval replaces the AV1 duration as soon as a chamber stimulating pulse is emitted. Sensing a spontaneous chamber reaction during the longer AV interval AV1 only results in that the longer AV interval is maintained.

In the embodiment described above, AA control has been used. In the pacemaker according to the invention, other control methods are however conceivable, such as VA control.

Although various minor changes and modifications might be suggested by those skilled in the art, it will be understood that I wish to include within the scope of the patent warranted hereon all such changes and modifications as reasonably come within my contribution to the art.

I claim as my invention:

1. A pacemaker, comprising:
   a first electrode lead means adapted to be disposed in an atrium of a heart for stimulating atrial reactions;
   a second electrode lead means adapted to be disposed in a chamber of the heart for stimulating and sensing chamber reactions;
   a stimulating pulse generator means for generating and emitting stimulating pulses to the atrium and the chamber via said first and second electrode lead means respectively; and
   a control device means for controlling the emission of the stimulating pulses and for the sensing of the chamber reactions, said control device means, after each emitted atrial stimulating pulse, starting an AV interval having a first duration, emitting a chamber stimulating pulse after expiration of the AV interval when no chamber reaction has been sensed during said AV interval, and, when the chamber stimulating pulse is emitted, replacing said first duration of said AV interval with a second duration which is shorter than said first duration.

2. A pacemaker according to claim 1 wherein the control device means, after switching to said second duration of said AV interval, replaces said second duration with said first duration if a chamber reaction is sensed during said second duration of said AV interval after the emission of an atrial stimulating pulse.

3. A pacemaker according to claim 1 wherein the control device means, after a predetermined number of consecutive chamber stimulating pulses, replaces said second duration of the AV interval with said first duration.

4. A pacemaker according to claim 1 wherein the control device means, after switching to said second duration of the AV interval, resets the AV interval to said first duration after a predetermined time.

5. A pacemaker according to claim 1 wherein the control device means sets the first duration of the AV interval between 240 and 260 ms, and the second duration of the AV interval between 140 and 190 ms.

6. A pacemaker, comprising:

a first electrode means adapted to be disposed in an atrium of a heart for stimulating atrial reaction;

a second electrode means adapted to be disposed in a chamber of the heart for stimulating and sensing chamber reactions;

a stimulating pulse generator means for generating and emitting stimulating pulses to the atrium and the chamber via the first and second electrode means; and a control device means for controlling the emission of the stimulating pulses and for the sensing of the chamber reactions, said control device means, after each emitted atrial stimulating pulse, starting an AV interval having a first duration, emitting a chamber stimulating pulse after expiration of the AV interval no chamber reaction has been sensed during the AV interval, when the chamber stimulating pulse is emitted replacing the first duration of the AV interval with a second duration which is shorter than the first duration, and changing back to the first duration from the second duration upon occurrence of a sensed event.

7. A pacemaker according to claim 6 wherein the event sensed by the control device means is one of the events selected from the group consisting of:

a chamber reaction during the second duration of the AV interval after the emission of an atrial stimulating pulse, sensing occurrence of a predetermined number of consecutive chamber stimulating pulses, and sensing of expiration of a predetermined time.

* * * * *